United States Patent
Lentzen et al.

(10) Patent No.: US 8,598,346 B2
(45) Date of Patent: Dec. 3, 2013

(54) SYNTHESIS OF CYCLIC AMIDINES

(75) Inventors: Georg Lentzen, Wesel (DE); Thorsten Neuhaus, Bochum (DE)

(73) Assignee: Bitop AG (DE)

( * ) Notice: Subject to any disclaimer, the term of this patent is extended or adjusted under 35 U.S.C. 154(b) by 148 days.

(21) Appl. No.: 13/003,862

(22) PCT Filed: Jul. 16, 2009

(86) PCT No.: PCT/EP2009/005175
§ 371 (c)(1),
(2), (4) Date: Mar. 16, 2011

(87) PCT Pub. No.: WO2010/006792
PCT Pub. Date: Jan. 21, 2010

(65) Prior Publication Data
US 2011/0178292 A1    Jul. 21, 2011

(30) Foreign Application Priority Data

Jul. 16, 2008    (DE) .................... 10 2008 033 448

(51) Int. Cl.
*A61P 17/00*    (2006.01)
*A61K 31/505*    (2006.01)
*C07D 233/18*    (2006.01)
*C07D 239/06*    (2006.01)
*C07D 243/04*    (2006.01)

(52) U.S. Cl.
USPC .......................................... 544/333; 544/335

(58) Field of Classification Search
USPC ................................ 544/333, 335
See application file for complete search history.

(56) References Cited

U.S. PATENT DOCUMENTS 5,789,414 A * 8/1998 Lapidot et al. ................ 514/256
2007/0243148 A1 * 10/2007 Andre et al. ................... 424/59

FOREIGN PATENT DOCUMENTS

FR    2860432    *    4/2005

OTHER PUBLICATIONS

Wei et al., A Natural Tetrahydropyrimidine Protects Small Bowel from Cold Ischemia and Subsequent Warm in vitro Reperfusion Injury, Pathobiology, vol. 76, No. 4, pp. 212-220, Jun. 2009.*
Oe et al., Short and Stereoselective Synthsis of Manzacidins A and C, and Their Enantiomers, Tetrahedron Letters, vol. 49, No. 52, pp. 7426-7429, Dec. 2008.*
Lanter et al., Asymmetric Aza-Mannich Reactions of Sulfinimines: Scope and Application to the Total Synthesis of a Bromopyrroile Alkaloid, Organic Letters, vol. 7, No. 26, pp. 5905-5907, 2005.*
Plate et al., Synthesis and in vitro Muscarinic Activities of a Series of 1,3-diazacycloalkyl Carboxaldehyde Oxime Derivatives, Bioorganic & Medicinal Chemistry, vol. 10, No. 4, pp. 1143-1152, 2002.*
Wei et al., A Natural Tetrahydropyrimidine Protects Small Bowel from Cold Ischemia and Subsequent Warm in vitro Reperfusion Injury, Pathobiology, vol. 76, No. 4, pp. 212-220, Jun. 2009.*
Cheng et al., Design and Synthesis of a Conformationally Restricted Cysteine Protease Inhibitor, Journal of Organic Chemistry, vol. 59, No. 25, pp. 7671-7676, 1994.*
CAPLUS printout of JP 03086867, Apr. 11, 1991.*
Brown et al., Hydropyrimidines. II. A New General Synthesis of Substituted 1,4,5,6-Tetrahydropyrimidines, Journal of the Chemical Society, pp. 4039-4045, 1962.*

* cited by examiner

*Primary Examiner* — Brenda Coleman
(74) *Attorney, Agent, or Firm* — Berliner & Associates

(57) ABSTRACT

The invention relates to an innovative method for synthesis of cyclic amidines. The synthesis starts from a β-, γ- or δ-lactone which is twofold brominated. After esterification of the carboxyl function, the bromine atoms are nucleophilically substituted and the corresponding diamino compound is obtained. The ring closure to the cyclic amidine is accomplished subsequently by reaction with orthoester, imidate or thioimidate. Owing to interposing additional steps for recovery of the diamino compound in enantiomerically pure form, the enantiomers of the cyclic amidines can be stereoselectively synthesized.

15 Claims, No Drawings

SYNTHESIS OF CYCLIC AMIDINES

This application is a national stage application filed under 35 U.S.C. 371 of PCT/EP2009/005175, filed Jul. 16, 2009.

The invention relates to a process for the preparation of cyclic amidines. The invention furthermore relates to various cyclic amidines themselves. In particular, the cyclic amidines concerned may be ectoine, ectoine derivates, and ectoine analogues.

Osmolytes and/or compatible solutes from extremophilic microorganisms constitute a well known group of low-molecular immunising substances. Extremophiles are very extraordinary microorganisms because they grow optimally and/or with high salt concentrations (up to 200 g NaCl/l) and high temperatures (60 to 110° C.), which in case of mesophilic (normal) organisms would lead to massive damage to cellular structures. In recent years, substantial research efforts have therefore been pursued to identify the biochemical components that lead to a remarkable stabilization of cell structures. Though a great deal of enzymes from hyperthermophilic microorganisms remain stable even under high temperatures, this cannot be generalized for cellular structures of thermophilic and hyperthermophilic organisms. Low-molecular organic substances (compatible solutes, osmolytes) in the intra-cellular environment render a substantial contribution to the high temperature stability of cell structures. Various novel osmolytes could be identified in recent years for the first time ever in extremophilic microorganisms. In some cases, it has already been managed to demonstrate the contribution rendered by these compounds to the protection of cellular structures—above all enzymes—against heat and dryness (K. Lippert, E. A. Galinski, *Appl. Microbiol. Biotech.* 1994, 37, 61-65; P. Louis, H. G. Trüper, E. A. Galinski, *Appl. Microbiol. Biotech.* 1994, 41, 684-688; Ramos et al., *Appl. Environm. Microbiol.* 1997, 63, 4020-4025; Da Costa, Santos, Galinski, *Adv. in Biochemical Engineering Biotechnology*, 61, 117-153).

For a lot of compatible solutes, sensible applications have come up and realized in the medical, cosmetic, and biological field. Reckoned to be among the most important compatible solutes is ectoine (1,4,5,6-tetrahydro-2-methyl-pyrimidine-4-carboxylic acid) and/or its derivatives. For example, EP 0 887 418 A2 describes the use of ectoine and hydroxyectoine to treat skin diseases or as an effective additive for cryoprotection of biological active ingredients and cells. DE 10 2006 056 766 A1 outlines the use of ectoines to treat the vascular leak syndrom (VLS). Further examples are the stabilization of vaccines (DE 100 65 986 A1), the treatment of pulmonary diseases due to the impact of suspended particulate matter and cardiovascular diseases (DE 103 30 768 A1) or the dermatological use to treat neurodermatitis (DE 103 30 243 A1).

Under high salt concentration conditions, compatible solutes like ectoines and hydroxyectoines can be enriched very well in bacteria like *halomonas elongata* or *marinococcus halophilus* and subsequently isolated from the dry mass. One possibility is the so-called "bacteria milking" method in which the salinity of a medium is decreased after the cells with high salinity have produced large quantities of ectoine. Decreasing the salinity causes the bacteria to sluice-out ectoine into the medium from which it can be isolated and chromatographically purified. The cells themselves remain intact and can be "milked" several times (T. Sauer, E. A. Galinski, *Biotech. Bioeng.*, 1998, 57, 306-313). The advantage of such a method as compared with a purely chemical synthesis in particular is the stereoselectivity of the biosynthesis. According to this method, merely the L ectoine in enantiomerically pure form is recovered. A disadvantage of biosynthesis, however, lies in that it is restricted to substances which are accumulated as end products in the bacteria themselves, i.e. a derivatization is at best possible in restricted extent proceeding from the recovered ectoine.

Known in principle, too, is a chemical synthesis of ectoine according to Koichi et al. (JP-A-03031265). According to this method, ortho-trimethyl acetate is reacted with 2,4-diaminobutyric acid. During the reaction, the 2.4 diaminobutyric acid is initially acetylated, and subsequently a condensing ring closure to the desired product is realized at elevated temperature.

Apart from ectoine and its derivates, corresponding 5- and 7-ring analogues are known, too. The corresponding 7-ring analogue is also designated as homoectoine (4,5,6,7-tetrahydro-2-methyl-1H-[1,3]-diazepine-4-carboxylic acid), calling the corresponding 5-ring analogue DHMICA (4,5-dihydro-2-methyl-imidazole-4-carboxylic acid). In conformity with the synthesis according to Koichi, homoectoine is obtained by ring closure between ortho-trimethyl acetate and ornithine, whereas DHMICA is obtained by ring closure between ortho-trimethyl acetate and 2,3-diamino propionic acid. In the course of initial investigations, homoectoine and DHMICA demonstrated promising properties.

However, there still does not exist a general synthesis approach to prepare different cyclic amidines which in their basic structure correspond to ectoine, homoectoine or DHMICA. Hence the task posed is to provide such a method.

This task is inventively solved by a method and process according to claim 1.

The inventive synthesis strategy starts from a lactone of the general formula II which is converted by bromination to a dibromine compound III. Bromination is accomplished in presence of bromine and PBr$_3$. Instead of a direct use of PBr$_3$ it is also possible to use phosphorous.

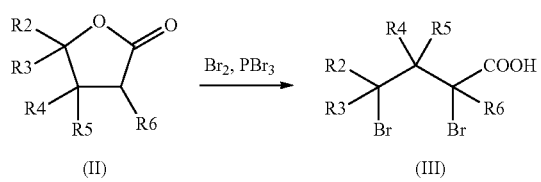

The 2,4-dibromine butyrate III obtained by bromination must be esterified for the subsequent reactions, thus getting to the corresponding ester IV of the 2,4-dibromine butyrate. Esterification is important on the one hand in view of follow-up reactions, and moreover esterification should be executed instantly, if possible, to prevent a formation of the corresponding α-bromine-γ-butyrolactones from the dibromine compound III under HBr-splitting-off. Esterification is preferably realized by reaction with methanol or ethanol in an acidic environment. Accordingly, esterification can be performed immediately after bromination, i.e. without any intermediate isolation of the compound III, for example by adding absolute methanol or ethanol under passage of gaseous hydrogen chloride HCl.

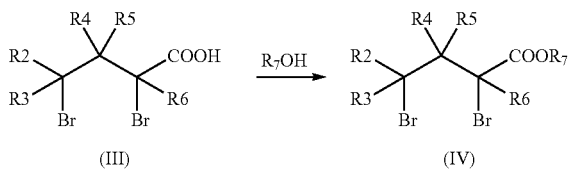

(III) → (IV)

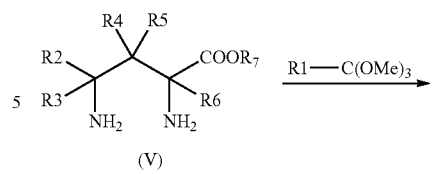

(V)

By a well-aimed variation of the substituent R2, R3, R4, R5 and R6 at the butyrolactone II, correspondingly substituted ectoine derivatives can be produced. The radicals R2, R3, R4, R5 and R6 may be H or optionally substituted alkyl, cycloalkyl, aryl, heteroaryl, alkylaryl, arylalkyl, alkoxyalkyl, alkylthioalkyl, aryloxyalkyl or arylthioalkyl radicals. A broad range of possible variations is thus available. Preferably, however, the radicals R2, R3, R4, R5 and R6 are H, $C_1$- to $C_6$-alkyl or aryl. Frequently a substitution will merely exist at one of the items R2, R3, R4, R5 and R6, whereas the other radicals represent an H atom.

Upon preparation of the esterified dibromine compound IV, amination to a diamino compound V is realized. Substitution of bromine by amino groups can be accomplished either by a direct reaction with ammonia or by a nucleophilic substitution with an azide followed by a subsequent hydrogenation. A direct reaction with ammonia can be accomplished in a concentrated aqueous ammonia solution at an elevated temperature of approx. 50° C. over an extended period of time of approx. 20 to 30 hours, by, reaction with ammonia in an autoclave or in liquid ammonia. For example, in the latter case, ammonia is condensed in a flask at approx. −40° C. and diluted with anhydrous ether, if required. The dibromine compound IV is slowly added. The reaction occurs over a period of approx. 2 hours.

Alternatively, a nucleophilic substitution of the bromine atoms can also be realized with an azide, preferably using sodium azide $NaN_3$. Subsequently, hydrogenation is carried out at standard conditions via an appropriate catalyst, for example palladium/activated carbon Pd/C or platinum.

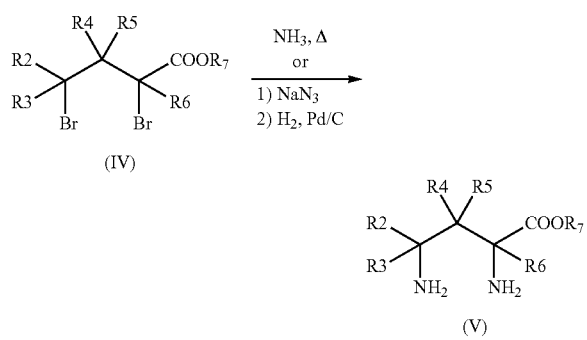

Finally, the diamino compound V thus obtained is cyclized to the desired product, possibly after previous hydrolysis of the ester function. In particular, this can be accomplished by reaction with a suitable ortho-ester R1-C(OR18)$_3$, with R1 again having the meaning and importance outlined hereinabove. R18 is an alkyl radical, more particularly a $C_1$-$C_6$-alkyl radical. The reaction is realized according to the general scheme as had been described by Koichi et al. (see above). Ortho-ester with R18=Me and R1=Me or Ph are obtainable on the market.

Instead of utilizing an ortho-ester, a reaction with an imidate or thioimidate is also conceivable. The reaction with a purchasable methyl acetimidate (R1=Me) and/or methyl benzimidate (R1=Ph) is illustrated in the following scheme and has been generally described by J. Einsiedel et al., *Bioorganic & Medicinal Chemistry Letters*, 2003, 13, 851-854.

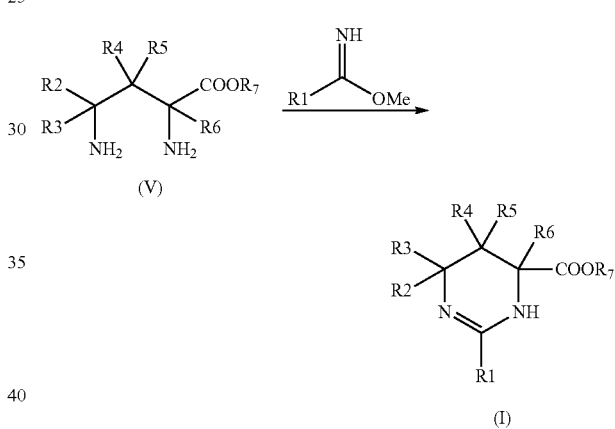

By utilizing an appropriate ortho-ester, imidate or thioimidate, the substituent R1 of the desired product can be adjusted. For example, by use of ortho-acetic acid trimethyl ester (trimethyl-orthoacetate, R1, 18=methyl), an ectoine derivative in which R1=methyl is generated, too.

As has been mentioned hereinabove, a hydrolysis of the ester function can also be accomplished prior to or after cyclization to amidine of the general formula I, i.e. R7=H upon completed hydrolysis, and it should be noted that—with a physiological pH—ectoine and its derivatives which dispose of a carboxyl function are present as zwitterion. As a matter of fact, the carboxy function can also be further derivatized by realizing an additional esterification. A broad range of possible variations is thus available to prepare different amidines of the general formula I.

Another viable derivatizing of the carboxy function lies in a conversion to amide. To this effect, in accordance with commonly known methods and processes, the product I, VI and/or XI is converted from a carboxylic acid and/or a carboxylic acid ester into a carboxylic acid amide. For example, this is accomplished by a direct conversion of ester or through an indirect route of reacting the corresponding acid chloride and/or anhydride with ammonia/an amine. Thus, compounds of the following basic structure are obtained:

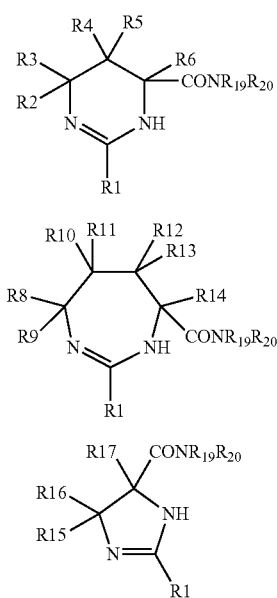

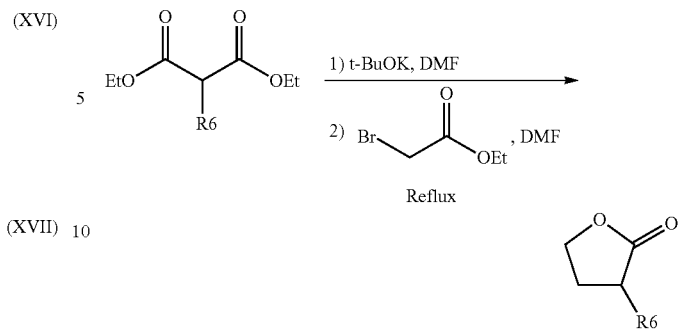

The preparation of butyrolactones with R5≠H is feasible, for example, in conformity with the following scheme:

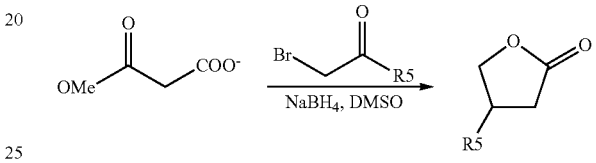

Further examples may be gathered from S. Schulz, *Liebigs Ann. Chem.* 1992, 8, 829-834.

In analogous manner, not only cyclical amidines with a 6-ring, but also those with a 5-ring or 7-ring can be produced, whose basic structure corresponds with that of the DHMICA and homoectoine, respectively. The reaction sequence corresponds with the sequence described hereinabove, though the basis to start from is not a γ-butyrolactone, but a β- and/or δ-lactone. This is turn is brominated and subsequently esterified. The bromine atoms are substituted by amino groups, and the ring closure is implemented subsequently by reaction with an ortho-ester, imidate, or thioimidate. The reaction conditions are by and large corresponding conditions, though the yield with the ring closure to a 7-ring empirically is worse, which is mainly attributable to the greater ring tension. In this manner, one obtains the 5-ring XI and/or 7-Ring VI. The reaction schemes are illustrated in the following:

Synthesis of the Homoectoine Derivative VI

Accordingly, R19 and R20 each can be H or alkyl, giving preference to R20=H. In particular, R19 can be a long-chain alkyl chain, for example $C_8$-, $C_9$-, $C_{10}$-, $C_{11}$-, $C_{12}$-, $C_{13}$-, $C_{14}$-, $C_{15}$-, $C_{16}$-, $C_{17}$- or $C_{18}$-. At the same time, R2-R6, R8-R14 and/or R15-R17 preferably is H, while R1 is equal to H or methyl, i.e. the rings mainly carry no further substituents. Amidines of this nature appear to be particularly promising due to the heightened lipophilicity.

The applied γ-butyrolactones are partly purchasable, for example R2=methyl, R3, R4, R5, R6=H (CAS: 108-29-2) or R2=phenyl, R3, R4, R5, R6=H (CAS: 1008-76-0), R2, R3, R4, R5=H, R6=methyl (CAS: 1679-47-6). Other lactones are not purchasable, but can be produced in accordance with the methods and processes described in the relevant literature. For example, WO 94/12487 A1 discloses the preparation of α-aryl-γ-butyrolactones. To this effect, an anion of the malonate as per the formula

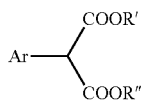

is reacted with an ethylene compound of the formula Y—CH₂—CH₂—OZ, with Y representing a leaving group such as tosylate or mesylate, and with Z representing a protective group, obtaining the compound

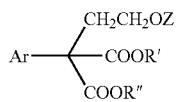

which under hydrolysis results in the desired lactone.

Other methods and processes which also start from malonates are described in B. Hoefgen et al., *J. med. Chem.*, 2006, 49, 760-769 or B. M. Nilsson et al., *J. med. Chem.* 1992, 35, 285-294. Butyrolactones with a substituent R6≠H can be illustrated, for example, in accordance with the following scheme:

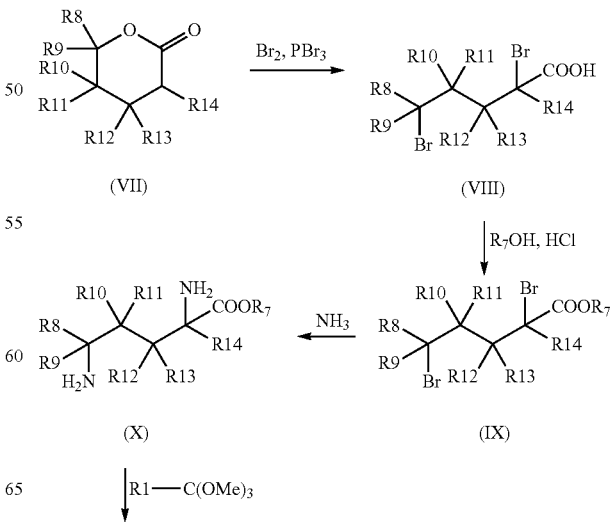

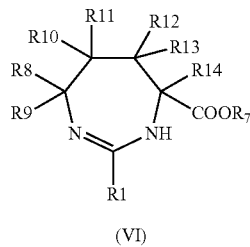

Synthesis of the DHMICA Derivative XI:

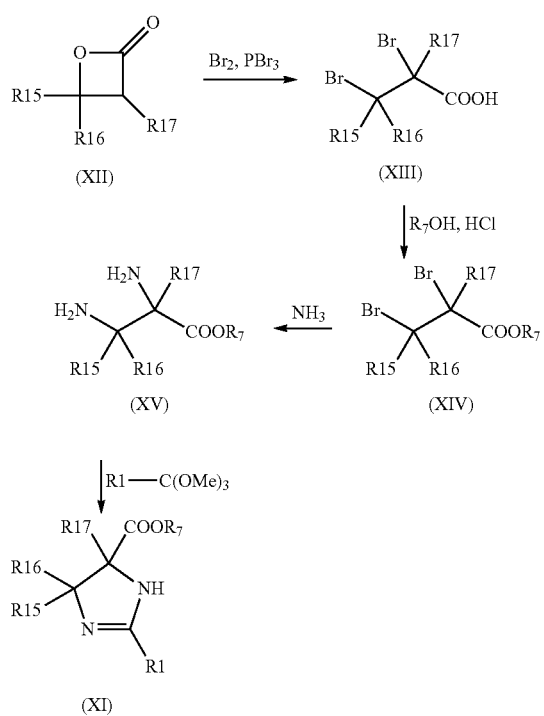

In conformity with a particularly advantageous variant of the inventive method, the cyclic amidines are recovered in an enantiomerically pure form. Hence, the compounds are the following ones:

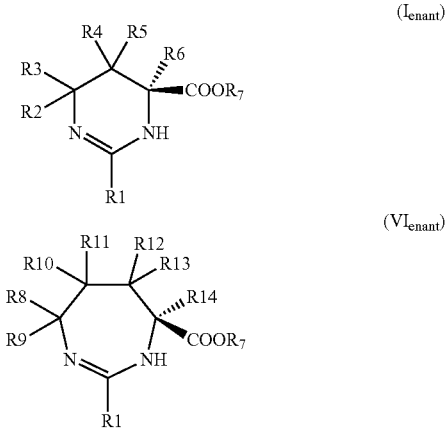

In particular, it can be the L-enantiomer so that for example the synthetically produced ectoine corresponds with the natural L-ectoine.

To prepare a cyclic amidine in enantiomerically pure form, the diamino compound V, X and/or XV is recovered in enantiomerically pure form and subsequently reacted as described above with an ortho-ester, imidate or thioimidate to obtain a cyclic amidine according to the formula I, VI or XI. The centre of chirality existing in the diamino compound is maintained.

Initially, the diamino compound is acylated at both amino functions, and subsequently a stereoselective monodeacylation is accomplished by the aid of an aminoacylase. Merely one enantiomer of the diacylated diamino compound is deacylated at one amino function, whereas the other enantiomer remains acylated at both amino functions. Enzymes suitable for this purpose, particularly those which merely hydrolyze the L-enantiomer of an amino acid are widely known. Of the two acylated amino groups, only the amino group in α-position is deacylated to the carboxyl group. After the reaction with the aminoacylase, it results a mixture composed of the monoacyl compound of the one enantiomer and the diacyl compound of the other enantiomer.

Subsequently, the diacyl compound of the non-desired enantiomer must be split-off. The remaining monacyl compound of the desired enantiomer is then hydrolyzed to the free diamino compound V, X and/or XV. Now, there is only one enantiomer of the diamino compound present, which in the following is designated as $V_{enant}$, $X_{enant}$ and/or. $XV_{enant}$. The further conversion to the desired, enantiomerically pure compound $I_{enant}$, $VI_{enant}$ oder $XI_{enant}$ is accomplished at described hereinabove. All embodiments for the preparation of cyclic amidines therefore in principle apply both to the use of the diamino compound V, X or XV as racemate or as enantiomer. Inasmuch as there is the talk of using an enantiomer, the optical purity may also be under 100%, though it is important that an enantiomer is substantially enriched as compared with the other enantiomer.

The acylation of the diamino compound V, X or XV in particular is an acetylation. Acylation can be carried out with usual acylating agents, for example by the aid of a carboxylic acid anhydride, a carboxylic acid chloride or a carboxylic acid bromide. Likewise, imidayolides or carboxylic acid thiolester as well as 2-pyridine thiolester can be utilized. Moreover, there are other methods and processes known according to prior art of technology in order to activate the acyl group of a carboxylic acid in such a manner that a reaction with an amino function to amide can be realized, for example the conversion with dicyclohexylcarbodiimide (DCC), 2-chlorine pyridinium or 3-chloroxazolium ions etc. Special preference in the case of acetylation is given to the application of acetic anhydride. This is realized in the usual manner in the alkaline range.

A selective mono-deacylation is accomplished by application of an amino acylase. These enzymes which belong to the family of hydrolases are capable of splitting-off the N-acyl group at the amino function of an amino acid, i.e. selectively with one enantiomer only. In most cases, the splitting-off is realized only with the L-enantiomer of the amino acid which is the enantiomer that mainly occurs in nature, whereas the D-enantiomer is not affected. Therefore, such amino acylases are also designated as N-acyl-L-amino acid amidohydrolase The use of acylase I, in particular of acylase I from *aspergillus*, is given special preference. This acylase is commercially obtainable, for example from the company Fluka, and it is also launched on the market in immobilized form on Eupergit. In addition, by means of the acylase I from *aspergillus*, only the acyl group at the amino function in α-position to the carboxyl group is split-off, whereas, for example, in case of the $N^\alpha,N^\gamma$-diacetyl-diaminobutyric acid, the acyl group at the γ-amino function is not affected.

However, there are D-amino acylases known, too, which selectively split-off only the N-acyl group with the D-enantiomer of an amino acid (vide e.g. C. S. Hsu et al., *Protein Sci.*, 2002, 11, 2545-2550). With the use of such an acylase, the L-enantiomer remains accordingly diacylated and can be split-off. In this manner, the inventive process provides a viable way to corresponding D-enantiomers of the cyclic amidines to be synthesized, particularly towards the D-ectoine, D-homoectoine, and D-DHMICA.

A separation of the diacylated non-desired enantiomer of the diamino compound is can be accomplished via a cation exchanger. To this effect, the solution is acidified with the amino acylase and the cation exchanger is washed with water. Subsequently, the desired enantiomer can be eluted in the alkaline range, for example with an $NH_3$-solution.

In order to subsequently liberate also the second amino function (in γ-, δ- or β-position) from the acyl group, a conventional method of the amide hydrolysis is employed, particularly by application of an acid or a base. Preference is given to splitting-off the acyl group in the acidic environment, for example by addition of HCl. The entire route to recover an enantiomer of a diamino compound is illustrated in the following by way of a 2.4 diaminobutyric acid. This acid is purchasable, but can also be obtained by applying the inventive method, with it being required to execute a hydrolysis of the ester function after preparation of the diamino compound.

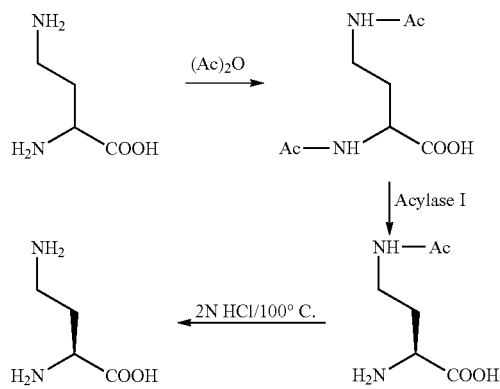

Apart from the inventive method, the invention also relates to cyclic amidines of the general formulae I, VI and XI as well as to salts derived hereof, except for the natural ectoine, homoectoine, and DHMICA itself as well as some other cyclic amidines which have already been described in the relevant literature. It is to be expected that the corresponding cyclic amidines will find applicability in medical, cosmetic or biological fields similarly to the applicability of ectoine or hydroxyectoine. This includes an application as active ingredient in skin care and as sun protection, the stabilization of cells, proteins, nucleic acids and biomembranes. To be named furthermore are the protection of cells, particular of skin cells, from stress factors such as heat, cold, UV radiation and dryness. By the aid of the inventive method, however, almost any differently functionalized ectoine, homoectoine and DHMICA derivatives can be produced, whose properties can be adapted depending on demand. For example, it is possible to integrate longer alkyl chains into the target structures I, VI and XI in order to increase the lipophilicity of the product. This in turn can improve its applicability in cosmetics. Though ectoine itself is excellently soluble in water which can be explained merely by its function as a compatible solute, in which ectoine gets enriched in high concentration in cytosol, but solubility in more richly lipophilic environments is restricted. Owing to the fact that the inventive method opens-up a broad range of possibilities for functionalization, the solubility of the ectoine derivative can be adjusted depending on demand.

Preferentially, the radicals R1 to R17 are H, $C_1$- to $C_6$-alkyl or aryl. In most cases, however, at least one substituent of the substituent couples R2-R3, R4-R5, R8-R9, R10-R11, R12-R13 and R15-R16 is =H. Frequently, a substitution will exist merely at one of the positions R1 to R17, whereas the other relevant radicals constitute an H atom.

Furthermore, special preference is given to such cyclic amidines of the general structure I, VI and XI, in which R7 is a long-chain alkyl radical, i.e. R7 preferably is a $C_8$-, $C_9$-, $C_{10}$-, $C_{11}$-, $C_{12}$-, $C_{13}$-, $C_{14}$-, $C_{15}$-, $C_{16}$-, $C_{17}$- or $C_{18}$-alkyl radical. At the same time, R2-R6, R8-R14 and/or R15-R17 preferably is H, whereas R1 is =H or methyl, i.e. the rings mainly carry no other substituents. On account of the increased lipophilicity, such amidines appear to be particularly promising.

In other preferred embodiments, the radical R1 constitutes a short-chain alkyl radical, particularly methyl, ethyl, n-propyl, isopropyl, n-butyl, sec-butyl, isobutyl or tert-butyl. At the same time, the radicals R2-R6, R8-R14 and/or R15-R17 as well as R7 preferably are again H, subject to the proviso that in this case R1 must not be methyl.

In accordance with another preferred embodiment, only one of the radicals R2-R5, R8-R13 and/or R15 or R16 each is =methyl, ethyl or phenyl, whereas the other radicals as well as R6, R14 and/or R17 are =H. At the same time, the following is preferentially valid for R1 and R7: R1 and R7=H; R1 and R7=methyl; R1=H and R7=methyl or R1=methyl and R7=H.

The invention furthermore also relates to cyclic amidines in enantiomerically pure form in which they can be produced according to the modified method described hereinabove. Thus, the cyclic amidine of the general formula I, VI or XI is preferably present as L-enantiomer, though it is also conceivable to exist as D-enantiomer which in terms of stereochemistry deviates from natural ectoine. Enantiomerics relates to the centre of chirality in α-position towards the carboxylic group. Accordingly, the L-enantiomer is the enantiomer which in terms of its stereochemistry corresponds to the natural ectoine ((S)-2-methyl-1,4,5,6-tetrahydro-4-pyrimidine carboxylic acid), with it being necessary to take into account that with a neutral pH value ectoine is present as zwitterion.

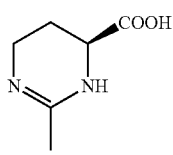

The following examples serve as a further explanation of the present invention:

EXAMPLE 1

Synthesis of methyl-2-4-dibromobutyrate
(2,4-dibromine butyric acid methyl ester 25 ml bromine were slowly added in droplets to a reheated mixture of phosphorous tribromide (0.83 ml) and γ-butyrolactone (42 g, 0.49 mol) at a temperature of 100 to 115° C. Subsequently, the mixture was reheated for another period of 30 min. The mixture was cooled in an icy bath, carefully adding 83 ml methanol and introducing gaseous HCl. The solution thus obtained was reheated for a period of 48 hours to 50° C. The volatile constituents were withdrawn, and the remaining oil was diluted with diethyl ester and washed two times with a 3%-rich aqueous sodium hydrogen carbonate solution and an NaCl solution. The washing solutions were re-extracted with diethyl ether and the unified organic phases were concentrated in a vacuum. Distillation at 0.2 torr resulted in the product methyl-2,4-dibromine butyrate in form of a colourless liquid (100.4 g, 80%).

EXAMPLE 2

Synthesis of 2,4-diamino butyric acid methyl ester

At a temperature of −40° C., 150 ml ammonia were condensed into a flask and diluted with 150 ml anhydrous diethyl ether. Slowly added to this solution were 100 g of 2,4-dibromine butyric acid methyl ester (0.385 mol) in 100 ml anhydrous diethyl ether. At a temperature of −40° C. stirring was continued for 2 hours, and subsequently it was slowly reheated to ambient temperature. After stirring over night, the ammonium bromide was filtered-off and the solvent was withdrawn. Obtained were 43.3 g (85%) 2,4-diamino butyric acid methyl ester.

EXAMPLE 3

Synthesis of 1,4,5,6-tetrahydro-2-methyl-pyrimidine-4-carboxylic acid methyl ester A solution of 2.4 g (0.018 mol) 2,4-diamino butyric acid methyl ester and 3.77 g ortho-acetic acid trimethyl ester in 50 ml dried methanol were reheated in the reflux for 24 hours. The solution was concentrated to dryness and the product was recrystallized from methanol/ethyl acetate. Obtained were 1.12 g (7.2 mmol, 40%) 1,4,5,6-tetrahydro-2-methyl-pyrimidine-4-carboxylic acid methyl ester.

EXAMPLE 4

Synthesis of L-2,4-diamino butyric acid

1) $N^\alpha,N^\gamma$-diacetyl-D,L-diamino butyric acid

Under stirring and ice cooling, acetic acid anhydride (1.42 ml; 15 mmol) and 7.5 ml 2 N NaOH were added in 5 portions to a solution of D,L-2,4-diamino butyric acid (955 mg; 5 mmol) in 7.5 ml 2 N NaOH. By adding 1.5 ml 2 N NaOH, the pH value was adjusted to 7.5. After 1 hour in ice, the solution was acidified with 2 ml 37% HCl to pH 3 and the aqueous phase was extracted 2 times with 50 ml n-butanol/ethyl acetate (2:1) each. After evaporating the organic phase in a vacuum to a small volume, precipitation was effected with methyl-tert-butylether Obtained were 800 mg (79%) $N^\alpha,N^\gamma$-diacetyl-D,L-diamino butyric acid as a colourless solid. DC: $R_f$=0.6 in acetonitrile/water/acetic acid (30:10:5); ESI-MS: m/z=203.05 $[M+H]^+$; $M_r$=202.21 calcld. for $C_8H_{14}N_2O_4$ 2) $N^\gamma$-acetyl-L-diamino butyric acid $N^\alpha,N^\gamma$-diacetyl-D,L-diamino butyric acid (404 mg; 2 mmol) were adulterated in 20 ml Sörensen-phosphate-buffer (1/15 molar) at pH 7.6 with 28 mg acylase I *aspergillus* (Fluka, 0.72 U7 mg enzyme; this corresponds to 10 U/1 mmol substrate) and incubated for 20 hours in a water bath at 40° C. The enzyme was separated by means of a membrane filter Amicon Ultra-4 (exclusion limit 10 kD) and the solution was adjusted with 1 N HCl to pH 2.5.

After feeding it to 50 ml cation exchanger Dowex 50Wx8 (50-100 mesh), washing was carried out with water having a pH value of up to 5 (separation of the diacetyl compound) and subsequently the desired product was eluted with 1 N ammonia. The eluate was evaporated in a vacuum, whereby colourless crystals of the $N^\gamma$-acetyl-L-diamino butyric acid developed instantly. Yield: 140 mg (88% of the expected 50%-rich yield); DC: $R_f$=0.3 mm acetonitrile/water/acetic acid (30:10:5); ESI-MS: m/z=161.10 $[M+H]^+$; $M_r$=160.17 calcld. for $C_6H_{12}N_2O_3$ 3) L-diamino butyric acid $N^\gamma$-acetyl-L-diamino butyric acid (140 mg; 0.87 mmol) were stirred in 10 ml 2 N HCl under reflux. Upon evaporation in vacuum, the crystalline residue was dissolved in as little water as possible and precipitated with 4 ml hot ethanol abs. The L-diamino butyric acid was obtained as monohydrochloride colourless. Yield: 125 mg (93%); DC: $R_f$=0.1 in acetonitrile/water/acetic acid (30:10:5); ESI-MS: m/z=119.08 $[M+H]^+$; $M_r$=118.14 calcld. for $C_4H_{10}N_2O_2$; $M_r$=154.60 calcld. for $C_4H_{10}N_2O_2 \times HCl$; $[\alpha]^{20}_D$=+24.4° (c=1.2 in 6 N HCl); Lit. (Beilstein, 4/IV, 2613): $[\alpha]^{21}_D$=+23.8° (c=1 in 6 N HCl); Fluka catalogue: $[\alpha]^{20}_D$=24±2° (c=1 in 6 N HCl). The enantiomer purity of the amino acid was confirmed and verified by means of derivatization with Marlfey's reagent (J. G. Adamson et al., *Anal. Biochem.*, 1992, 202, 210-214) and a subsequent HPLC. Conditions: Column ET 125/4 Nucleosil 100-5 C8 (Macherey and Nagel, Düren); linear gradient from eluent A (1% trifluoroacetic acid (TFA) in $H_2O$) to eluent B (0.8% TFA in acetonitrile); $R_t$=15.6 min.

The invention claimed is:
1. Method for preparation of cyclic amidines of formula I

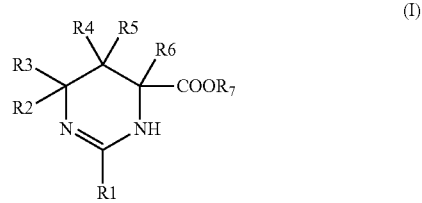

with R1, R2, R3, R4, R5, R6, $R_7$=H, optionally substituted alkyl, cycloalkyl, aryl, heteroaryl, alkylaryl, arylalkyl, alkoxyalkyl, alkylthioalkyl, aryloxyalkyl or arylthioalkyl comprised of the following steps:
bromination of a lactone of formula II

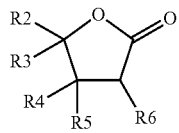
(II)

to a dibromine compound of formula III

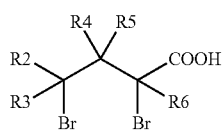
(III)

esterification of the dibromine compound III to a compound IV

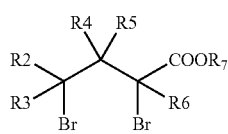
(IV)

amination of the dibromine compound IV to a diamino compound V

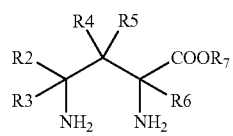
(V)

and
reaction of the compound V with an ortho-ester of formula $R1\text{-}C(OR_{18})_3$, with R1 having the meaning and importance outlined hereinabove and $R_{18}$=alkyl, or an imidate of formula

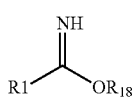

with R1, $R_{18}$ having the meaning and importance as outlined hereinabove, or a thioimidate of formula

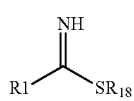

with R1, $R_{18}$ having the meaning and importance as outlined hereinabove, to obtain a cyclic amidine of formula I.

2. Method according to claim 1, characterized in that the ester function of the compound V is hydrolyzed prior to the step of the reaction with orthoester, imidate or thioimidate.

3. Method according to claim 1, characterized in that the amination of the dibromine compound IV is realized by reaction with an azide and a subsequent hydrogenation.

4. Method according to claim 1, characterized in that the amination of the dibromine compound IV is realized by reaction with $NH_3$.

5. Method according to claim 1, characterized in that R1-6 and $R_7$ are =H, $C_1$- to $C_6$-alkyl or aryl.

6. Method according to claim 1, characterized in that at least one substituent of the substituent couples R2-R3 and R4-R5 is =H.

7. Method according to claim 1, characterized in that the carboxylic acid or carboxylic acid ester function $COOR_7$ is converted to a carboxylic acid amide function $CONR_{19}R_{20}$, with $R_{19}$ and $R_{20}$ being =H or alkyl.

8. Method according to claim 1, characterized by the following additional steps to recover an enantiomer of compound V:
acylation of compound V at both amino functions to a diacyl compound
stereoselective monodeacylation of an enantiomer of the diacyl compound in α-position by application of an amino acylase to a monoacyl compound
separation of the non-deacylated diacyl compound, and
hydrolysis of the monoacyl compound to the enantiomer of compound V.

9. Method according to claim 8, characterized in that the enantiomer is the L-enantiomer.

10. Method according to claim 8, characterized in that the acyl group is an acetyl group.

11. Method according to claim 8, characterized in that the amino acylase is an acylase I from *aspergillus*.

12. Cyclic amidine of the formula I as well as its salts

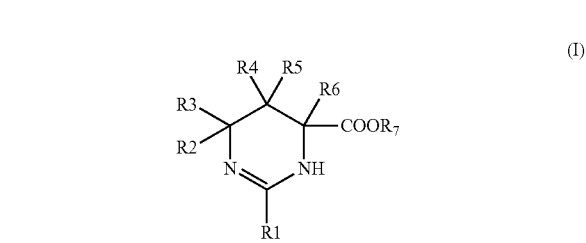
(I)

with $R_7=C_8$-, $C_9$-, $C_{10}$-, $C_{11}$-, $C_{13}$-, $C_{14}$-, $C_{15}$-, $C_{16}$-, $C_{17}$- or $C_{18}$-alkyl, R1=either H or methyl and R2, R3, R4, R5, R6=H.

13. Cyclic amidine according to claim 12, characterized in that the amidine is present as L- or D-enantiomer.

14. Cyclic amidine of formula XVI as well as its salts

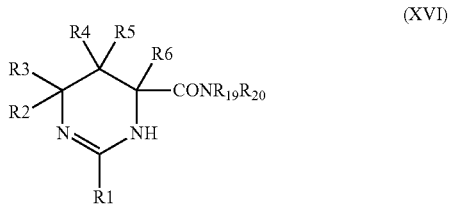
(XVI)

with $R_{19}=C_8$-, $C_9$-, $C_{10}$-, $C_{11}$-, $C_{12}$-, $C_{13}$-, $C_{14}$-, $C_{15}$-, $C_{16}$-, $C_{17}$- or $C_{18}$-alkyl, R2, R3, R4, R5, R6 and $R_{20}$ being =H and with R1 being =H or methyl.

15. Method according to claim 1, characterized in that $R_{18}$ is $C_1$-$C_6$-alkyl.

* * * * *